(12) United States Patent
Anderson et al.

(10) Patent No.: US 11,599,999 B2
(45) Date of Patent: Mar. 7, 2023

(54) APPARATUS, SYSTEM, AND METHOD FOR FLUORESCENCE IMAGING WITH STRAY LIGHT REDUCTION

(71) Applicant: Verily Life Sciences LLC, South San Francisco, CA (US)

(72) Inventors: Brian Anderson, Mountain View, CA (US); Tamara Troy, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 283 days.

(21) Appl. No.: 17/166,382

(22) Filed: Feb. 3, 2021

(65) Prior Publication Data

US 2022/0245794 A1 Aug. 4, 2022

(51) Int. Cl.
*G06K 9/00* (2022.01)
*G06T 7/00* (2017.01)
(Continued)

(52) U.S. Cl.
CPC ............ *G06T 7/0012* (2013.01); *A61B 1/043* (2013.01); *A61B 1/0669* (2013.01);
(Continued)

(58) Field of Classification Search
CPC ....... G06T 7/0012; G06T 7/90; G06T 11/001; G06T 2207/10064; G06T 5/008; G06T 2207/10016; G06T 2207/10068; G06T 2207/10152; G06T 2207/30168; A61B 1/043; A61B 1/0669; A61B 5/007;
(Continued)

(56) References Cited

U.S. PATENT DOCUMENTS 7,179,222 B2 2/2007 Imaizumi et al.
8,451,328 B2 5/2013 Yoshino et al.
(Continued)

OTHER PUBLICATIONS

Alander et al. "A Review of Indocyanine Green Fluorescent Imaging in Surgery", International Journal of Biomedical Imaging, vol. 2012, Sep. 1, 2012.
(Continued)

*Primary Examiner* — Tom Y Lu
(74) *Attorney, Agent, or Firm* — Christensen O'Connor; Johnson Kindness PLLC

(57) ABSTRACT

An apparatus, system, and method for fluorescence imaging with stray light reduction is described. The system including a light source to provide a first illumination of a scene to induce fluorescence from the scene, an image sensor to capture a fluorescence image of the scene during the first illumination, and a controller coupled to the light source, the image sensor, and memory that includes instructions that when executed by the controller causes the system to perform operations. The operations including comparing a first color channel value to a second color channel value of a given pixel included in the fluorescence image to identify one or more pixels of the fluorescence image as being affected by stray light. The operations further including generating a stray light image mask based, at least in part, on the one or more pixels of the fluorescence image identified as being affected by the stray light.

21 Claims, 11 Drawing Sheets

(51) Int. Cl.
  *G06T 7/90* (2017.01)
  *G06T 11/00* (2006.01)
  *A61B 1/04* (2006.01)
  *A61B 1/06* (2006.01)
  *A61B 5/00* (2006.01)
(52) U.S. Cl.
  CPC .......... *A61B 5/0071* (2013.01); *A61B 5/0084* (2013.01); *G06T 7/90* (2017.01); *G06T 11/001* (2013.01); *G06T 2207/10064* (2013.01)
(58) Field of Classification Search
  CPC ....... A61B 5/0084; A61B 1/05; A61B 1/0684; A61B 1/00009
  See application file for complete search history.

(56) References Cited

U.S. PATENT DOCUMENTS

| | | |
|---|---|---|
| 9,143,746 B2 | 9/2015 | Westwick et al. |
| 9,407,838 B2 | 8/2016 | Butte et al. |
| 10,524,644 B2 | 1/2020 | Scott et al. |
| 10,902,572 B1* | 1/2021 | Kennedy .................. G06T 7/30 |
| 2003/0001104 A1* | 1/2003 | Sendai ................. A61B 5/0071 |
| | | 250/458.1 |
| 2013/0317371 A1* | 11/2013 | Takei ................... A61B 5/0084 |
| | | 600/476 |
| 2017/0020377 A1* | 1/2017 | Takeuchi ........... A61B 1/00006 |
| 2018/0000401 A1* | 1/2018 | Kang ..................... A61B 1/063 |
| 2018/0234603 A1* | 8/2018 | Moore ................. H04N 5/2256 |
| 2019/0041333 A1* | 2/2019 | Doser .................. A61B 5/0071 |
| 2019/0216325 A1 | 7/2019 | Ouyang |
| 2019/0379840 A1 | 12/2019 | Frangioni |

OTHER PUBLICATIONS

International Search Report and Written Opinion, dated Mar. 22, 2022 in corresponding International Patent Application No. PCT/US2021/065020, 8 pages.

\* cited by examiner

```
mask_image =
        max(ir[red] - ir[blue], 0.0)

smooth_mask =
        gaussian_filter(mask_image, sigma=8)
```

APPARATUS, SYSTEM, AND METHOD FOR FLUORESCENCE IMAGING WITH STRAY LIGHT REDUCTION

TECHNICAL FIELD

This disclosure relates generally to the field of fluorescence imaging, and in particular but not exclusively, relates to stray light reduction for fluorescence imaging.

BACKGROUND INFORMATION

Fluorescence imaging is an imaging technique that utilizes fluorophores for a variety of applications, such as visualizing biological processes (e.g., dynamics of gene expression, protein expression, molecular interactions, and the like), DNA sequencing, cancer detection, marking or tracking biological features, and the like. The fluorophore is a fluorescent chemical compound that can re-emit light upon illumination by excitation light. Specifically, upon illumination by the excitation light, the illuminated molecules of the fluorophore absorb the excitation light, briefly enter a higher energy state (e.g., excited state), and subsequently emit fluorescence light when the molecules return to a ground energy state. The fluorescence light can be captured or otherwise imaged by an image sensor for applications as described above and as follows. In one example, indocyanine green (ICG) is a fluorescent dye used for medical diagnostics applications. In another example, ICG can be used as a tracer or marker during surgery. One use case is during a cholecystectomy, ICG may be used to distinguish between the bile duct and an artery to assist a surgeon during removal of a gallbladder.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of an apparatus, system, and method for fluorescence imaging with stray light reduction are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In general, embodiments of the present disclosure are described in context of fluorescence imaging using an endoscope in a surgical setting. However, it should be appreciated that the techniques and embodiments described herein are generally applicable to the field of fluorescence imaging and corresponding image processing techniques and thus should not be deemed limited to only endoscopic fluorescence imaging and/or surgical settings. For example, techniques described herein may be used for image processing of fluorescence images. In the same or other embodiments, fluorescence imaging may be utilized outside of a surgical setting. Additionally, one of ordinary skill in the art will appreciate that fluorescence imaging covers the span of a variety of areas including, but not limited to, microscopy, imaging probes, spectroscopy, and the like.

Figure 1A:
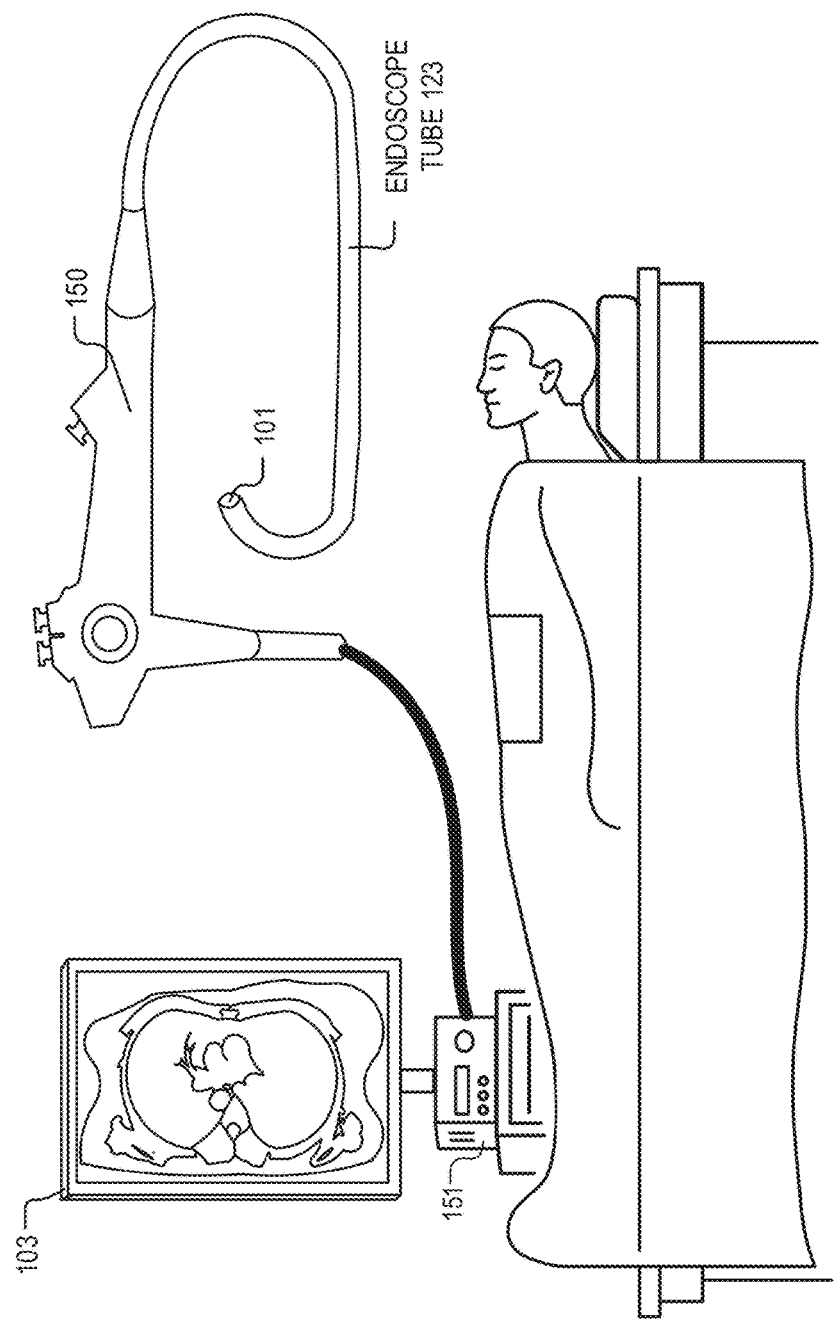
FIG. 1A illustrates an example fluorescence imaging system with stray light reduction, in accordance with an embodiment of the disclosure.

FIG. 1A illustrates an example fluorescence imaging system 100 with stray light reduction, in accordance with an embodiment of the disclosure. System 100 includes an endoscope 150 (with distal tip 101 of endoscope tube 123) coupled to controller 151 to output, on display 103, images or videos of a scene (e.g., an internal or external view of the operating patient) in real-time. For example, system 100 may alternate between capturing a fluorescence image and a color image of the scene to enable a user to view, in substantially real-time, a combined color image showing both fluorescence, which typically occurs outside of the visible wavelength range of light, and a color image. The controller 151 may implement various image processing techniques described herein to reduce the effect of stray light on the fluorescence image.

As shown, the proximal (hand-held) end of the endoscope 150 may have a number of buttons or joysticks to control movement of distal tip 101. One of ordinary skill in the art will appreciate that endoscope 150 depicted here is merely a cartoon illustration of an endoscope, and that the term "endoscopy" should encompass all types of endoscopy (e.g., laparoscopy, bronchoscopy, cystoscopy, a colonoscopy, sigmoidoscopy, thoracoscopy, laryngoscopy, angioscopy, arthroscopy, robotic surgery, or any other situation when a camera or optical probe is inserted into a body), and that an endoscope should include at least "chip-on-a-tip" devices, rod lens devices (ridged), image fiber devices (flexible), and the like. It is further appreciated that endoscope 150 may also be included in or otherwise coupled to a surgical robotic system.

Figure 1B:
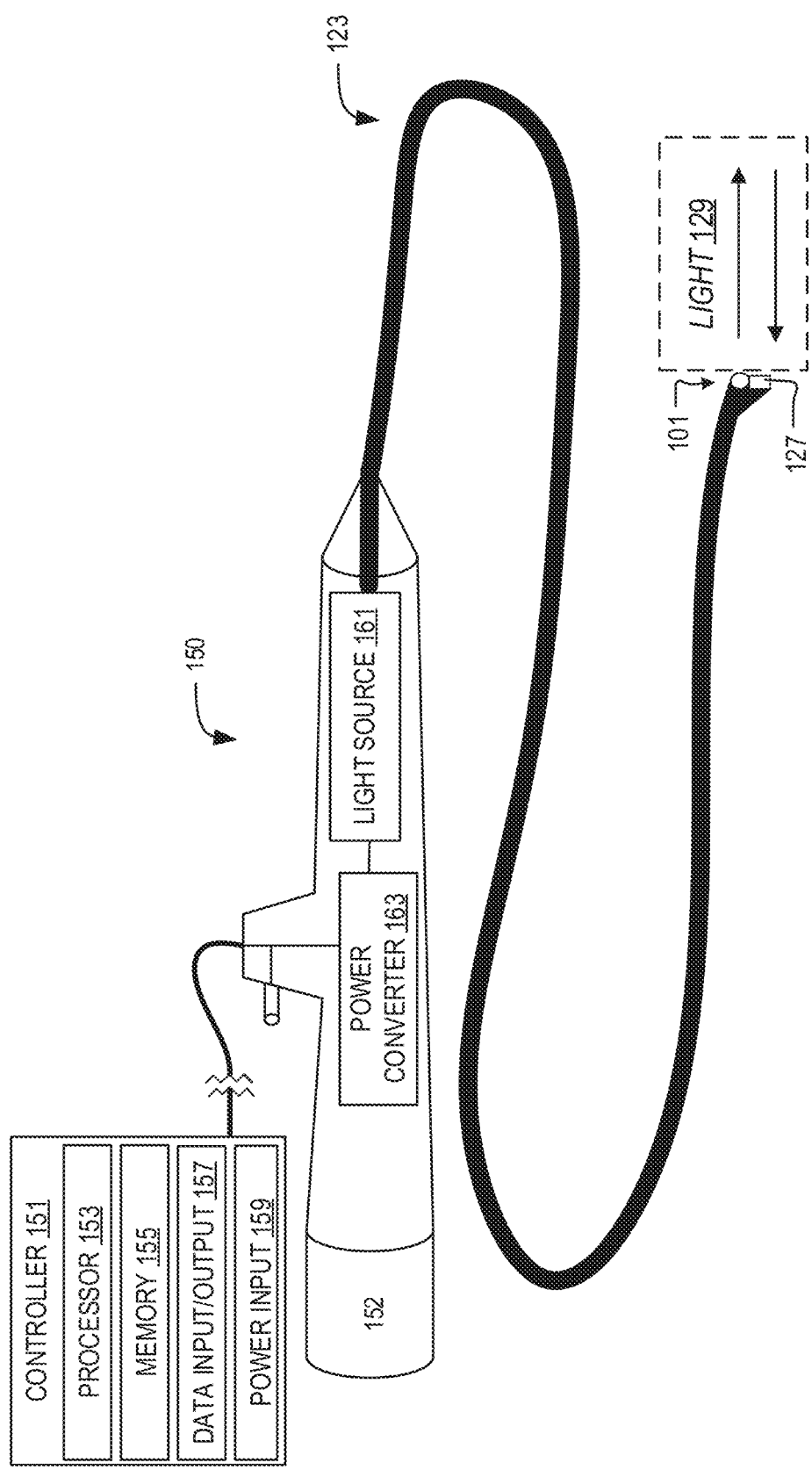
FIG. 1B illustrates an example endoscope which may be used in the fluorescence imaging system of FIG. 1A, in accordance with an embodiment of the disclosure.

FIG. 1B illustrates the example endoscope 150 which may be used in the fluorescence imaging system 100 of FIG. 1A, in accordance with an embodiment of the disclosure. Referring back to FIG. 1B, endoscope 150 includes endoscope tube 123, an image sensor positioned proximate to a distal end 101 of the endoscope tube 123, a light source 161, and a power converter 153. Endoscope 150 is coupled to controller 151, which includes processor 153, memory 155, data input/output 157, and power input 159.

Endoscope 150 includes a proximal end (to be hand-held or mounted) and a distal end (end of endoscope tube 123 closest to image sensor 127) to be inserted into a patient receiving the surgical procedure. Light source 231 (e.g., one or more light emitting diodes, laser diodes, and the like) is optically coupled to the proximal end of endoscope tube 123 to emit or receive light 129. More specifically, one or more optical fibers may be bundled within the endoscope tube 123 to optically couple the light source 161 with the distal end 101 of the endoscope tube to allow for the distal end to be positioned within the patient and illuminate the scene (e.g. surgical site). Image sensor 127 is coupled to the distal end of the endoscope tube 123 and positioned to receive light 129 (e.g., light that has reflected off the scene or light that has been fluoresced from the scene) to capture images and/or videos representative of the scene.

It is appreciated that in some embodiments the image sensor may not be disposed proximate to the distal end 101 of the endoscope tube 123. Rather, in some embodiments, the image sensor 127 may be disposed within housing 152 of endoscope 150 or elsewhere within the system. In one embodiment, endoscope 150 may include a plurality of optical fibers, disposed within the endoscope tube 123, with a first portion of the optical fibers coupled to light source 161 to direct light from light source 161 through the endoscope tube 123 and out the distal end 101 and a second portion of the optical fibers coupled to the image sensor 127 to direct light received at the distal end 101 through the endoscope tube 123 and to the image sensor 127.

Controller 151 may be disposed internal (e.g., disposed with housing 152) or external (e.g. wired or wirelessly connected) to endoscope 150. Controller 151 includes a processor 153, storage 155 (e.g., any non-transitory computer-readable storage medium or machine accessible storage medium), data input/output 157 (e.g., to send/receive the images and/or videos from image sensor 127), and power input 159 (e.g., to power endoscope 150). Data input/output 157 may include an input apparatus coupled to controller 151. The input apparatus may be positioned to receive an input command from an operator (e.g. the surgeon). In response to receiving the input command, the endoscope may perform fluorescence imaging with a reduced influence from stray light. The controller 151 is coupled to the light source 161, the image sensor 127, and memory 155. The memory includes instructions that when executed by the controller causes the system (e.g., fluorescence imaging system 100 of FIG. 1A) to perform operations for fluorescence imaging with a reduced influence from stray light.

It is appreciated that the controller 151 may orchestrate operation of the fluorescence imaging system 100 of FIG. 1A and includes software (e.g., instructions included in memory 155 coupled to processor 153) and/or hardware logic (e.g., application specific integrated circuits, field-programmable gate arrays, and the like) that when executed by controller 151 causes the system 100 of FIG. 1A to perform operations for fluorescence imaging with stray light reduction, in accordance with embodiments of the disclosure.

Figure 2A:
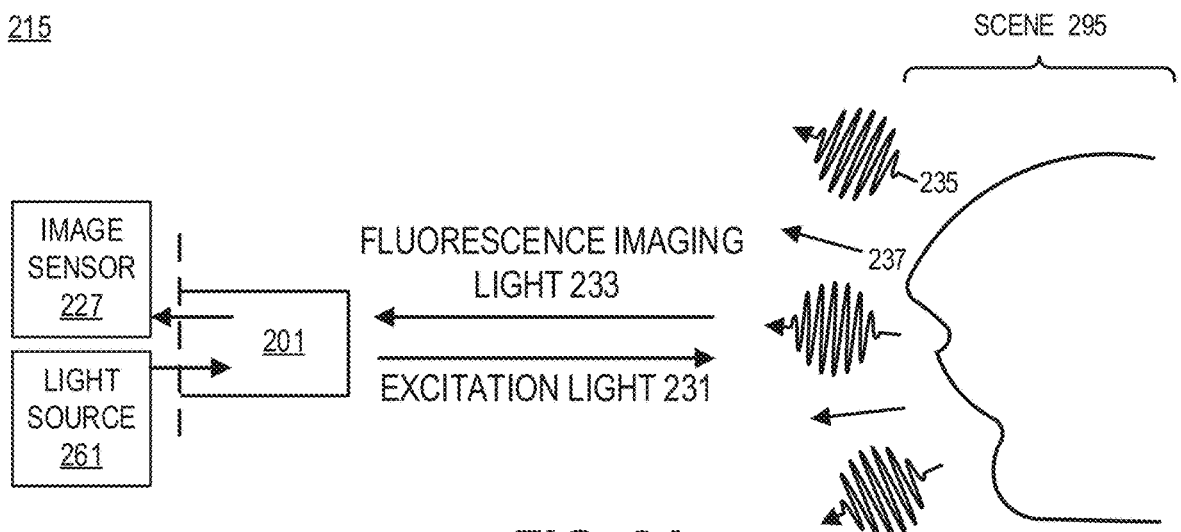
FIG. 2A illustrates an example scenario for capturing a fluorescence image with an image sensor, in accordance with an embodiment of the disclosure.

FIG. 2A illustrates an example scenario 215 for capturing a fluorescence image with an image sensor 227, in accordance with an embodiment of the disclosure. More specifically, a distal tip 201 of an endoscope (e.g., endoscope 150 of fluorescence imaging system 100 of FIG. 1A and FIG. 1B) is positioned to illuminate a scene 295 with light source 261 and subsequently image the scene 295 via image sensor 227. It is appreciated that distal tip 201, image sensor 227, and light source 261 may correspond to the like named elements illustrated in FIG. 1A and FIG. 1B. Referring back to FIG. 2A, light source 261 is configured (e.g., by adjusting a power to one or more lasers included in the light source 261) to provide a first illumination of the scene 295 by emitting excitation light 231. The excitation light 231 includes an excitation wavelength (e.g., 800 nm or any other wavelength that induces fluorescence based on the chemical composition of fluorophores included in the scene 295) that induces fluorescence 235 from the scene 295 as the fluorophores within the scene 295 transition from an excited energy state caused by the first illumination to a ground energy state. Additionally, the excitation light 231 may reflect from the scene 295 in the form of stray light 235.

As illustrated in the depicted embodiment, the image sensor 227 receives fluorescence imaging light 233 to capture a fluorescence image representative of the scene 295 during the first illumination. In some embodiments, it is appreciated that the fluorescence image may be referred to as an infrared (IR) image as the wavelength of the fluorescence 235 included in the fluorescence imaging light 233 may be in the IR or near-IR regime. However, the fluorescence imaging light 233 may include both the fluorescence 235 emitted from the scene and the stray light 237. The stray light 237 may have a similar or greater intensity than the fluorescence 235 and result in degradation of the fluorescence image (e.g., in the form of halos, glare, or other optical aberrations). In some embodiments, an optical filter (see, e.g., optical filter 280 illustrated in FIG. 2C) may be placed between the image sensor 227 and the fluorescence imaging light 233 to prevent the majority of the stray light 237 from reaching the image sensor 227 since fluorescence intensity is typically about 100 times less than the excitation light 231. However, even if an optical filter is used, said filter may not be perfectly matched to prevent all stray light 237 from reaching the image sensor 227 (e.g., the excitation light 231 may reflect off the scene 295 in a manner that causes the reflected light to be incident upon the image sensor 231 off axis or otherwise at a high angle that bypasses the filter). Accordingly, it is highly desirable to have an algorithmic approach to complement the optical filter to further reduce the influence of the stray light 237.

Figure 2B:
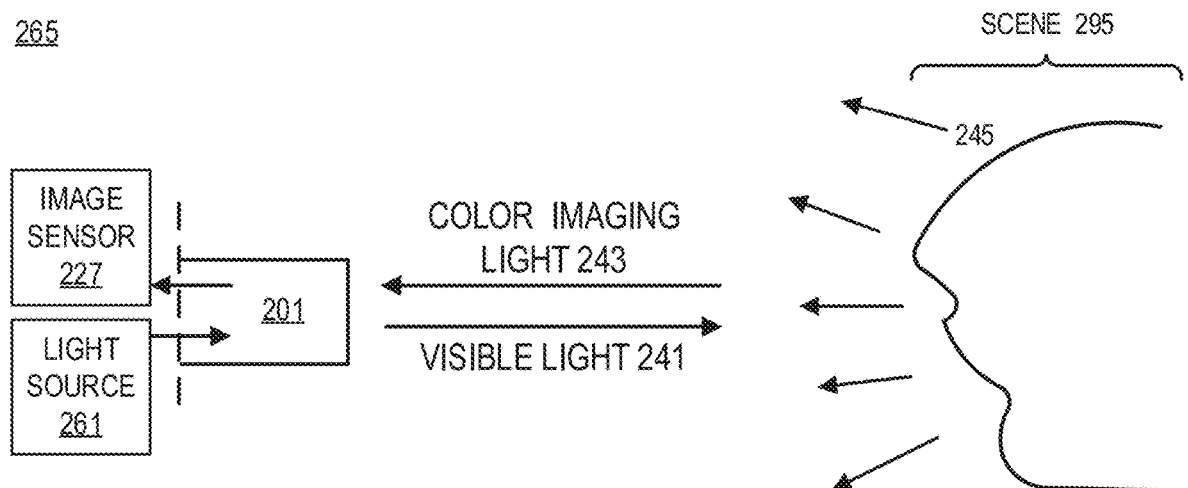
FIG. 2B illustrates an example scenario for capturing a color image with the same image sensor as FIG. 2A, in accordance with an embodiment of the disclosure.

FIG. 2B illustrates an example scenario 265 for capturing a color image with the same image sensor 227 as FIG. 2A, in accordance with an embodiment of the disclosure. The color image may be captured in sequence with the fluorescence image (e.g., to generate a combined color image showing fluorescence from the scene 295). As illustrated in FIG. 2A, the light source 261 provides a second illumination of the scene 295 by configuring the light source 261 to emit visible light 241 (e.g., providing power to one or more light emitting diodes, laser diodes, or the like with wavelengths within the visible spectrum of light). The visible light 241 subsequently reflects from the scene 295 in the form of reflected visible light 245 that can be captured as color imaging light 243 by the image sensor 227. In some embodiments, visible light may include a light with a wavelength between 380 nm and 750 nm. For example, light source 261 may include a plurality of laser diodes (e.g., a combination of a 450 nm laser, a 520 nm laser, a 550 nm laser, and a 635 nm) that may be powered or otherwise activated simultaneously to simulate white light for color imaging of the scene 295.

Figure 2C:
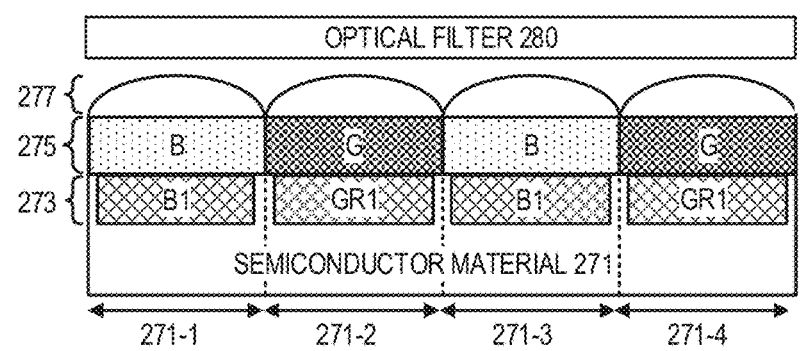
FIG. 2C and FIG. 2D illustrates an example image sensor for fluorescence imaging, in accordance with an embodiment of the disclosure.

FIG. 2C illustrates a cross-section of example image sensor 227 for fluorescence imaging, in accordance with an embodiment of the disclosure. As illustrated, image sensor 227 includes a semiconductor material 271 (e.g., silicon), a plurality of photodiodes 273 disposed within the semiconductor material 271, a color filter 275, a plurality of microlenses 277, and an optical filter 280 (e.g., a notch filter, a band-stop filter, or other filter configured to block or attenuate light that would otherwise be incident upon the image sensor). The image sensor includes multiple subpixel types dependent upon the color filter 275 (e.g., red, green, and blue subpixel types when the color filter 275 is a Bayer pattern). For example, subpixel 271-1 is a blue subpixel type and subpixel 271-2 is a green subpixel type.

Figure 2D:
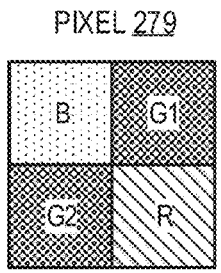

FIG. 2D illustrates a pixel 279 of the image sensor 227 illustrated in FIG. 2C, in accordance with an embodiment of the disclosure. As illustrated in FIG. 2D, pixel 279 is a full-color or "macro" pixel that includes a group of subpixels (e.g., a minimal repeat unit of the subpixels included in image sensor 227) that are capable of collectively capturing the visible range of the electromagnetic spectrum (e.g., visible light). As illustrated, pixel 279 includes a blue subpixel (B), a red subpixel (R), a first green subpixel (G1), and a second green subpixel (G2), which correspond to a minimal repeat unit of subpixels included in the image sensor 227. However, it is appreciated that the illustrated arrangement of subpixels and other components of the image sensor 227 should not be deemed limiting and that other arrangements or components may be used.

Figure 3A:
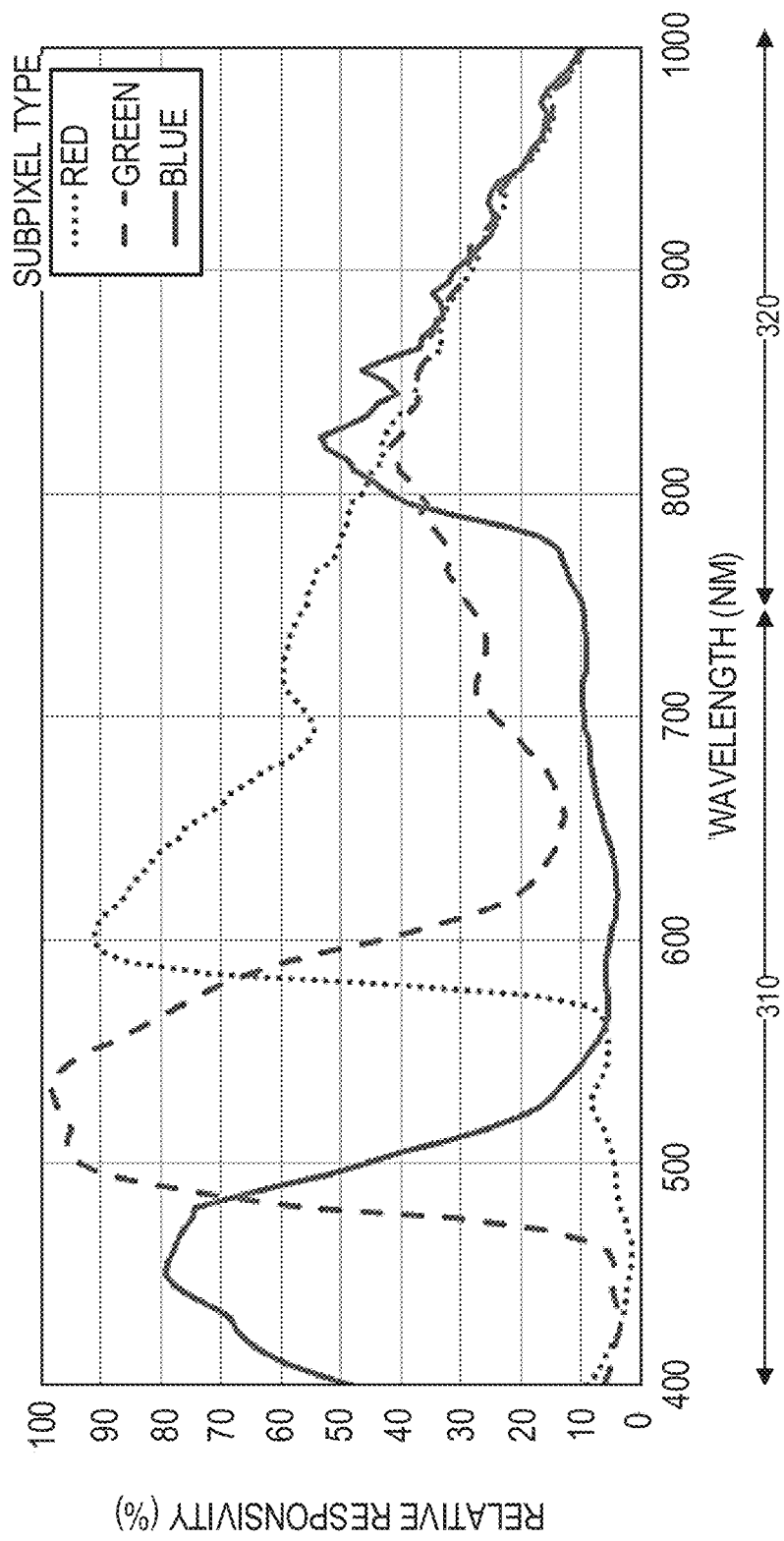
FIG. 3A illustrates an example responsivity chart of subpixel types included in an image sensor, in accordance with an embodiment of the disclosure.

FIG. 3A illustrates an example responsivity chart 300 of subpixel types included in an image sensor, in accordance with an embodiment of the disclosure. Responsivity chart 300 is a non-limiting example of responsivity for the image sensor 127 included in FIG. 1B and image sensor 227 included in FIGS. 2A-2D. As illustrated in FIG. 3A, the responsivity of the image sensor is dependent on the color pixel type with the greatest responsivity for a given subpixel type being within its respective color band within the visible range 310 of the electromagnetic spectrum (e.g., red subpixel types have greatest responsivity to red light, green subpixel types have greatest responsivity to green light, and blue subpixel types have greatest responsivity to blue light).

As illustrated in FIG. 3A, responsivity for non-visible light (e.g., infrared light 320) is not zero for the image sensor. In other words, the image sensor is capable of generating infrared images in the absence of visible light or by using a filter that attenuates or blocks visible light. In the context of fluorescence imaging, a scene (e.g., scene 295 of FIG. 2A and FIG. 2B), may be encapsulated or otherwise shielded from outside light such that a light source (e.g., light source 161 of FIG. 1B or light source 261 of FIG. 2A and FIG. 2B) is the only source of illumination to enable the image sensor to capture fluorescence images where the wavelength of fluorescence may span from visible to infrared light. However, it is noted that the excitation light that induces fluorescence may also be in the infrared range 320 (e.g., 800 nm), which may subsequently reflect from the scene and be absorbed by the image sensor as stray light since responsivity of the image sensor within the infrared range 320 is non-zero.

Figure 3B:
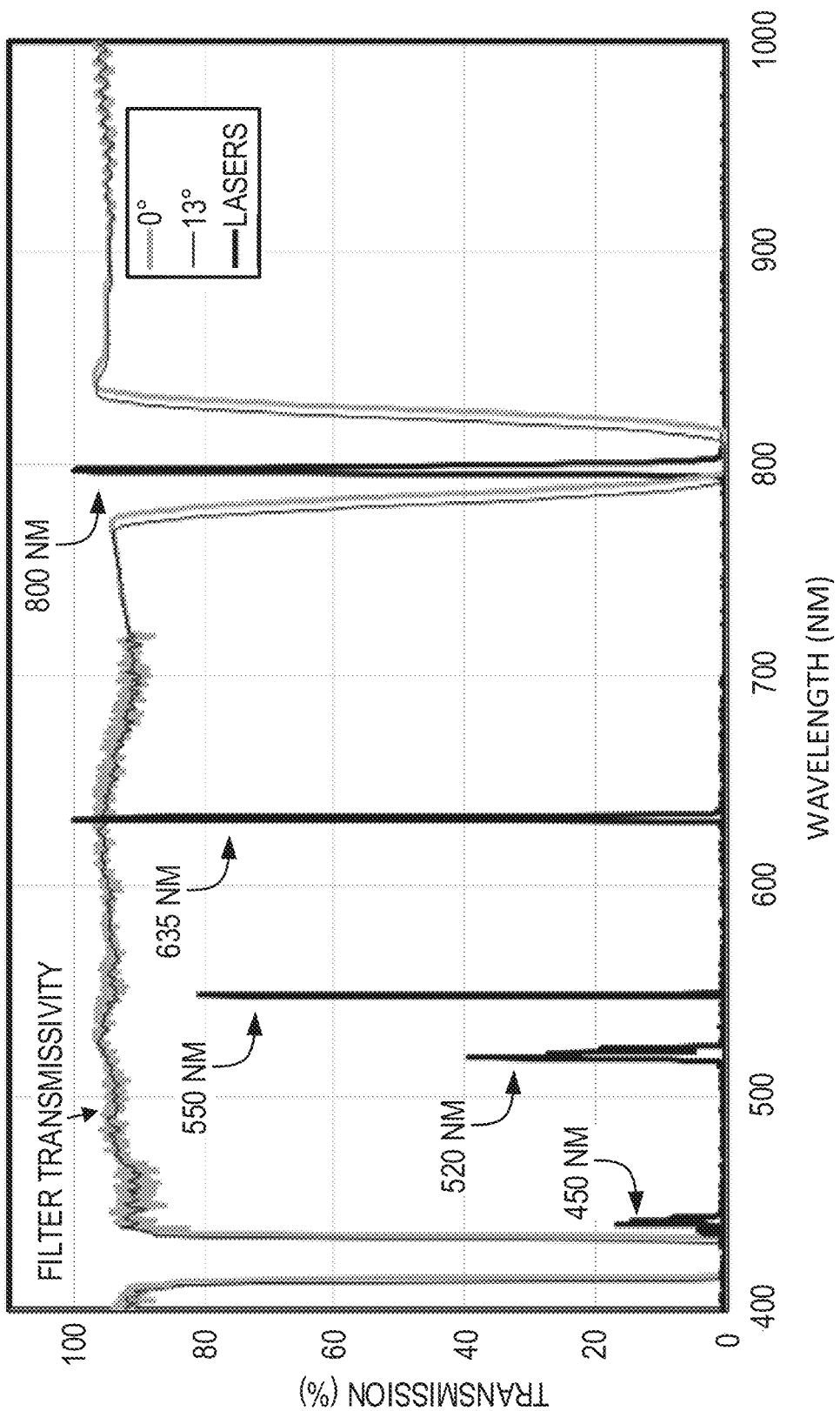
FIG. 3B illustrates an example transmissivity chart of an optical filter coupled to an image sensor of a fluorescence imaging system with respect to emission spectra of a light source, in accordance with an embodiment of the disclosure.

FIG. 3B illustrates an example transmissivity chart for an optical filter (e.g., optical filter 280 illustrated in FIG. 2C) coupled to an image sensor (e.g., image sensor 127 of FIG. 1 and/or image sensor 227 of FIG. 2A-2D) of a fluorescence imaging system with respect to emission spectra of a light source (light source 161 of FIG. 1B and/or light source 261 of FIG. 2A and FIG. 2B), in accordance with an embodiment of the disclosure. Importantly, the filter illustrated in FIG. 3B allows for substantial transmission (e.g., greater than 80%, greater than 90%, or the like) of light within the visible range of the electromagnetic spectrum (e.g., lasers with wavelengths of approximately 450 nm, 520 nm, 550 nm, and 635 nm) to enable color imaging of the scene. For wavelengths outside of the visible range, the filter has a transmissivity profile that substantially attenuates light within a narrow wavelength range that includes the excitation light. For example, when the excitation light includes an excitation wavelength of 800 nm to induce fluorescence of the scene, the filter has a transmissivity that substantially attenuates light proximate to the excitation wavelength (e.g., reduce transmissivity to zero or near-zero). In other words, light that is incident upon the filter that has a wavelength within 10%, 5%, 1% or is otherwise proximate to the excitation wavelength is substantially attenuated to near-zero or zero. However, the filter may not be perfectly matched or able to compensate for all stray light (e.g., excitation light that reflects at an off angle from the scene).

Figure 3C:
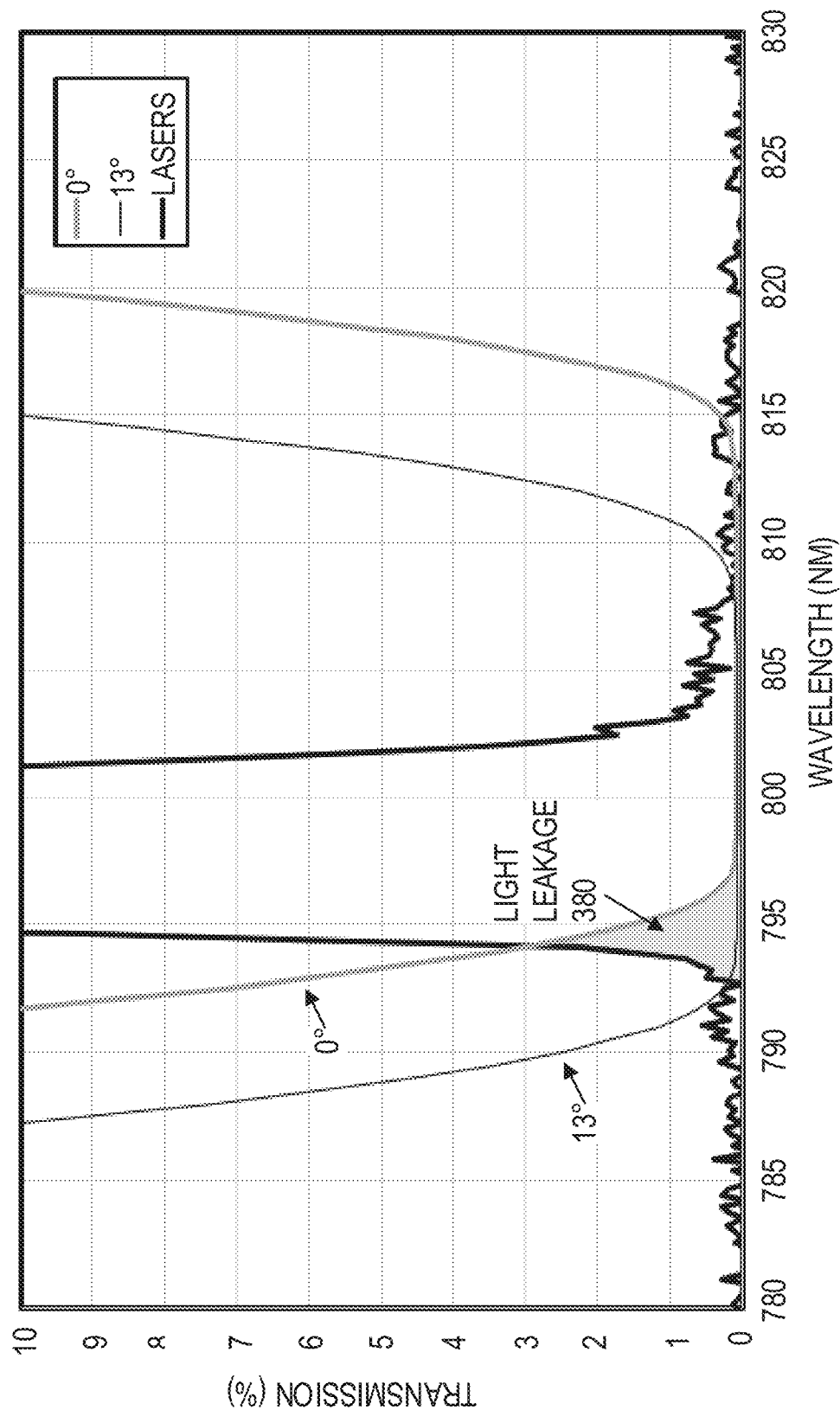
FIG. 3C illustrates a zoomed in view of the example transmissivity chart of FIG. 3B to show example light leakage due to mismatch between the optical filter and the light source, in accordance with an embodiment of the disclosure.

FIG. 3C illustrates a zoomed in view of the example transmissivity chart of FIG. 3B to show example light leakage 380 caused by mismatch between the optical filter and the light source, in accordance with an embodiment of the disclosure. More specifically, the zoomed in view shows a laser included in the light source with an excitation wavelength of approximately 800 nm with respect to transmissivity of the optical filter for light with a zero degree angle of incidence (labeled as "0°") and a thirteen degree of angle of incident (labeled as "13°"). As illustrated, there is a slight mismatch between the optical filter and the laser which allows for light leakage 380 that corresponds to a portion of light from the laser at approximately 795 nm when the light has a zero degree angle of incidence.

Figure 3D:
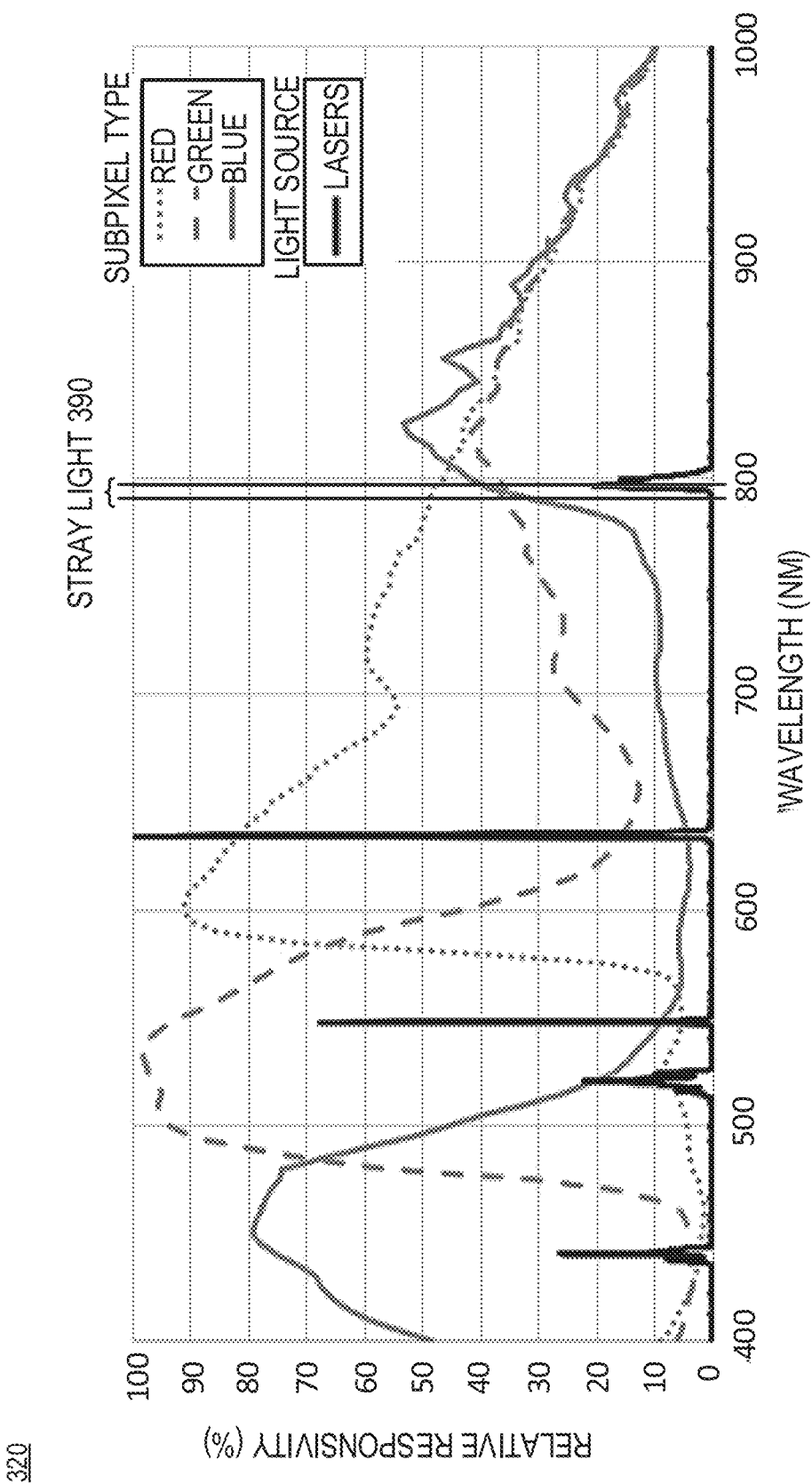
FIG. 3D illustrates an example responsivity chart showing stray light affecting images captured by an image sensor included in a fluorescence imaging system, in accordance with an embodiment of the disclosure.

FIG. 3D illustrates an example responsivity chart 320 showing stray light affecting images captured by an image sensor included in a fluorescence imaging system, in accordance with an embodiment of the disclosure. More specifically, chart 320 corresponds to the relative responsivity chart 300 of FIG. 3A with respect to the emission spectra of the light source shown in FIG. 3B. Referring back to FIG. 3D, stray light 390 may be captured or otherwise imaged by the image sensor associated with the responsivity chart 320 when the laser with the 800 nm emission peck is active due to mismatch with the optical filter.

However, it is appreciated that there is a spectral sensitivity difference between the subpixel types of the image sensor and the stray light 390, which is utilized in accordance with embodiments of the disclosure to generate a fluorescence image with a reduced impact from the stray light 390. As illustrated, the red subpixel type has a greater sensitivity to the stray light 390 than the green or blue subpixel types. Thus, in the illustrated embodiment, the red subpixel type is a dominant subpixel type of the image sensor with respect to the stray light 390. Consequently, when intensity values of red subpixel are greater than the blue or green subpixel types there is an indication that the corresponding image pixel will be affected by the stray light 390 when capturing a fluorescence image. However, when capturing a fluorescence image, the stray light is considered noise in a signal where the fluorescence is targeted for imaging. In some embodiments, it is likely the green subpixel type will have the highest overall intensity or strongest signal based on the image sensor being used (e.g., an image sensor with a Bayer color filter pattern has two times the of green subpixels as red or blue subpixels). Therefore, in one or more embodiments, the green color channel values may be used to generate a single color channel fluorescence image and the spectral sensitivity difference of the image sensor (e.g., based on the difference between the red and blue color channel values) can be used to determine whether or not a particular image pixel of the single color channel fluorescence image is affected by stray light.

Figure 3E:
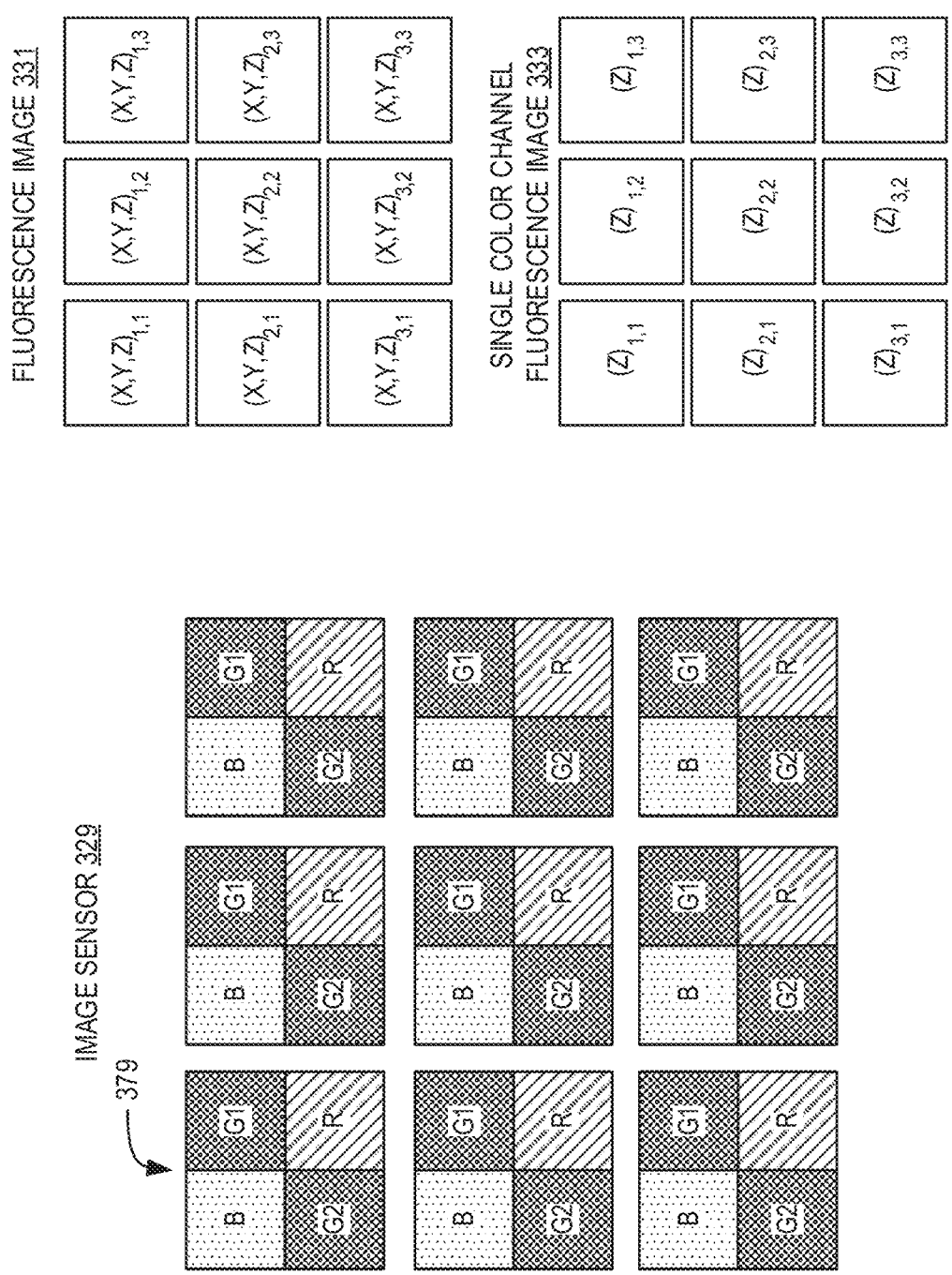
FIG. 3E illustrates a schematic of an image sensor and a corresponding fluorescence image captured by the image sensor when imaging a fluorescing scene, in accordance with an embodiment of the disclosure.

FIG. 3E illustrates a schematic of an image sensor 329 and a corresponding fluorescence image 331 captured by the image sensor 329 when imaging a fluorescing scene, in accordance with an embodiment of the disclosure. Image sensor 329 is one possible implementation of image sensor 129 illustrated in FIG. 1B and/or image sensor 229 illustrated in FIGS. 2B-2D. For the sake of discussion, image sensor 329 has a responsivity similar to the responsivity chart 300 illustrated in FIG. 3A and the fluorescence image 331 is representative of a scene illuminated by a light source with an excitation wavelength of approximately 800 nm to induce fluorescence from the scene. Fluorescence image 331 includes multiple color channels and is representative of the scene during the illumination that induces the fluorescence. Single color channel fluorescence image 333 includes a single color channel and is based on the fluorescence image 331.

In the illustrated embodiment, image sensor 329 includes a plurality of pixels 379 arranged in an array or grid (e.g., array with three rows and three columns, for example), with each pixel including a group of subpixels (e.g., one blue subpixel, one red subpixel, and two green subpixels) to form a full color image pixel or "macro" pixel. As discussed above in relation to FIG. 3D, the red subpixel types of this image sensor have a greater responsivity to stray light (e.g., excitation light reflected off the scene towards the image sensor) than at least one other subpixel type. In the same or other embodiments, the red subpixel type may be a dominant subpixel type that has a greater responsivity to stray light than any other subpixel type included in the image sensor (e.g., the blue and green subpixel types). Consequently, the color channel values of the fluorescence image 331 is indicative of the spectral variance of the image sensor 329. Each image pixel of the fluorescence image 331 is representative of a spatially corresponding pixel 379 of the image sensor 329. For example, the image pixel in the first row and column of fluorescence image 331 is spatially associated with the pixel 379 in the first row and column of the image sensor 329. Each image pixel included in the fluorescence image 331 have color channel values denoted as X, Y, Z based on the number of different subpixel types of the image sensor (e.g., the first color channel value is a red color channel, denoted as "X", and is associated with an intensity measured by a corresponding "R" subpixel, the second color channel is a blue color channel, denoted as "Y", and is associated with an intensity measured by a corresponding "B" subpixel, and the third color channel is a green color channel, denoted as "Z", and is associated with an average of the intensity measured by the corresponding "G1" and "G2" subpixels).

As discussed above, the sensitivity of subpixel types to stray light is dependent upon the responsivity of a given subpixel type of the image sensor. More specifically and in this specific embodiment, the dominant subpixel type most responsive to the excitation light is the red subpixel type based on the responsivity chart of FIG. 3D. Thus, if the red color channel value has a value greater than either one of the blue or green color channel values for a given image pixel (e.g., X is greater than Z for the image pixel in row 1 and column 1), then the given image pixel is likely affected by stray light.

In some embodiments, the fluorescence image 331 will be utilized to generate a single color channel fluorescence image 333 based on one of the color channels of the fluorescence image 331. In the same embodiment, the other color channels of the fluorescence image 331 are used to determine whether a given pixel of the fluorescence image 331 (and thus a corresponding one of the pixels of the single color channel fluorescence image 333) is affected by the stray light, which can subsequently be corrected. In one embodiment, the single color channel fluorescence image 333 is based on the third color channel values of the fluorescence image 331 (e.g., the green color channel denoted as "Z"). Then, the first color channel ("X") and the second color channel value ("Y") are compared to one another to determine whether a given pixel is affected by the stray light. For example, if X is greater than Y for the given pixel in the first row and column ("1,1") of the fluorescence image 331, then the given pixel is expected to be affected by stray light. Consequently, the corresponding pixel in the first row and column of the single color channel fluorescence image 333 is also expected to be affected by the stray light. The corresponding pixel of the single color channel fluorescence image 333 may then be corrected based on a difference between the first color channel value and the second color channel value of the spatially associated pixel of fluorescence image 331. In some embodiments, the one or more pixels identified as being affected by the stray light may be corrected based on the spectral sensitivity variance of the image sensor. For example, the corrected value of the pixel in the first row and column of the single color channel fluorescence image 331 may correspond to $Z+n(X-Y)$, based on a stray light image mask as discussed in relation to method 400 of FIG. 4A-4D, if the pixel is identified as being affected by stray light. In such an embodiment, n may correspond to a value that scales the influence of the difference between X and Y. In some embodiment, n may be a user configurable value that may be determined or otherwise adjusted empirically. In other embodiments, pixels may be corrected based on a ratio between the first color channel and the second color channel. In some embodiments, the difference between the first color channel value and the second color channel value may be scaled, normalized, or otherwise adjusted.

Figure 4A:
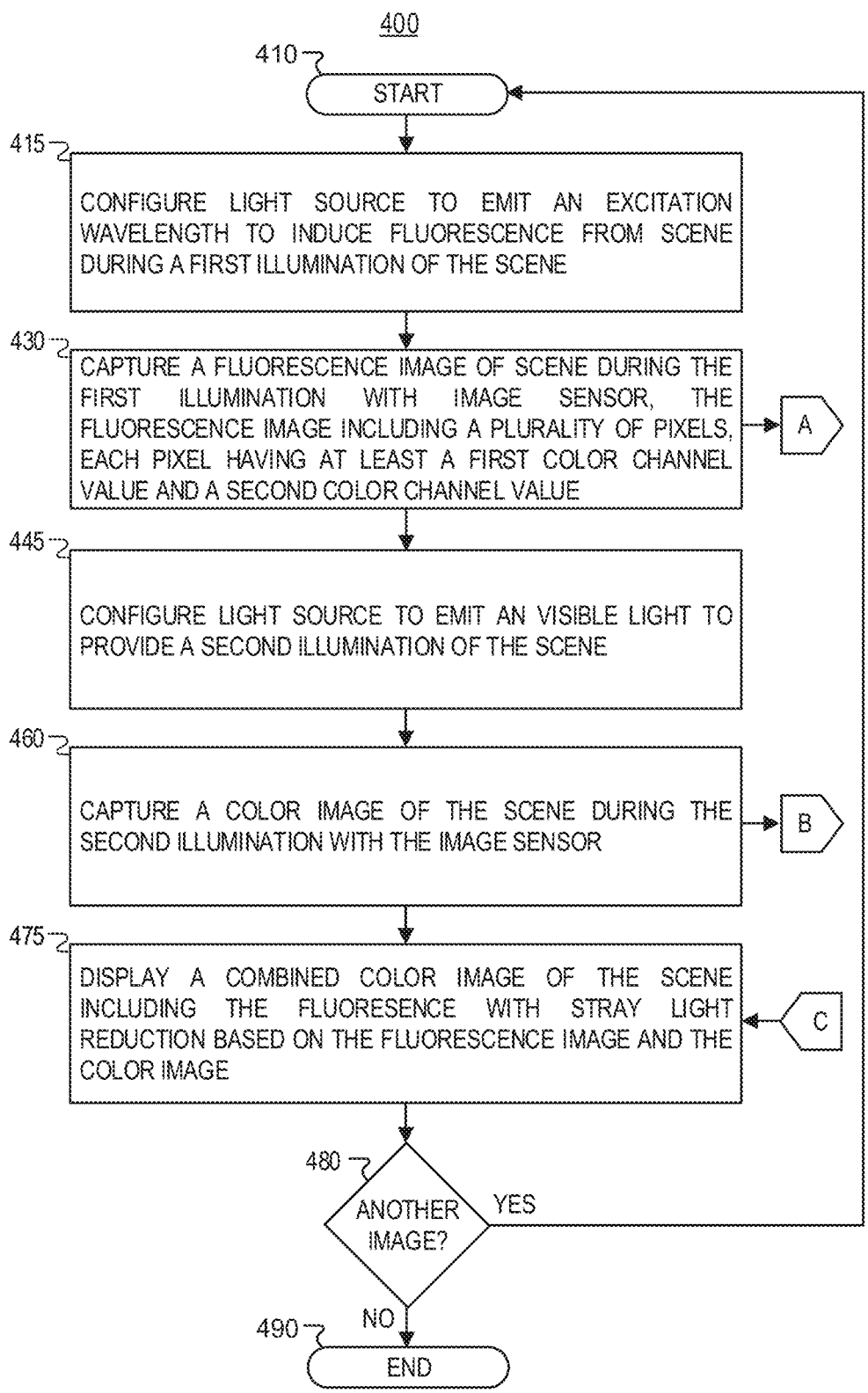
FIG. 4A illustrates an example method for fluorescence imaging with a reduced influence from stray light, in accordance with an embodiment of the disclosure.

FIG. 4A illustrates an example method 400 for fluorescence imaging with a reduced influence from stray light, in accordance with an embodiment of the disclosure. Method 400 includes process blocks 410-490 illustrated in FIG. 4A-4D and may be implemented by fluorescence imaging system 100 illustrated in FIG. 1A to utilize the spectral sensitivity variance of an image sensor to reduce the influence of stray light during fluorescence imaging. In the same or other embodiments, method 400 may be included as instructions provided by at least one machine-accessible storage medium (e.g., non-transitory memory) that, when executed by a machine, will cause the machine to perform operations for fluorescence imaging with a reduced influence from stray light. It is further appreciated that the order in which some or all of the process blocks appear in method 400 should not be deemed limiting. Rather, one of ordinary skill in the art having the benefit of the present disclosure will understand that some of the process blocks may be executed in a variety of orders not illustrated, or even in parallel.

Block 410 illustrates initiating method 400 and may correspond to a user pressing a button of fluorescence imaging system (e.g., depressing a button of endoscope 150 illustrated in FIG. 1A-1B) to indicate that an endoscope tube is in position and for fluorescence imaging of a scene to begin. In the same or other embodiments, the system may be automated such that user interaction is not required to commence initialization of the fluorescence imaging or corresponding image processing.

Block 415 shows providing a first illumination of the scene by configuring the light source to emit an excitation wavelength to induce fluorescence from the scene. The light source may be configured by providing power to activate an appropriate laser, light emitting diode, or other light emitting source with an excitation wavelength sufficient to induce fluorescence from the scene. It is appreciated that in some embodiments, the only light source incident upon the scene is the first illumination that includes the excitation wavelength. In other words, the scene may be encapsulated or otherwise sealed such that background light is minimal and the only substantial radiation source illuminating the scene is excitation light emitted from the light source and the fluorescence emitted from the scene.

Block 430 illustrates capturing, with an image sensor, a fluorescence image of the scene during the first illumination. Accordingly, the fluorescence image is representative of the fluorescence emitted from the scene but may also be influenced by stray light (e.g., the excitation light reflecting from the scene to be incident upon the image sensor). The fluorescence image includes a plurality of pixels (e.g., fluorescence image 331 illustrated in FIG. 3D), each pixel having at least a first color channel value (e.g., a red color channel value) and a second color channel value (e.g., a blue color channel value). In some embodiments, the fluorescence image may have additional or different color channel values (e.g., a green color channel).

Block 445 shows providing a second illumination of the scene by configuring the light source to emit visible light. The light source may be configured by powering a plurality of light emitting lasers or diodes included in the light source (e.g., red light, green light, and blue light as illustrated in FIG. 3C and FIG. 3D) to simulate white light. Accordingly, the visible light may be broad spectrum that spans the visible range, discrete spectra within the visible range (e.g., multiple lasers with different narrow band spectra), or other light that may be illuminated simultaneously or sequentially for generating a color image of the scene. It is appreciated that in some embodiments the excitation source may also illuminate the scene during the second illumination.

Block 460 illustrates capturing a color image of the scene during the second illumination. It is appreciated that the same image sensor utilized to capture the fluorescence image may also be used to capture the color image of the scene. Accordingly, the color image may be spatially associated with the fluorescence image. For example, a pixel in column 1 and row 1 of the fluorescence image and the color image may both be representative of the same spatial portion of the scene.

Block 475 shows displaying a combined color image of the scene including the fluorescence with stray light reduction based on the fluorescence image and the color image. The combined color image be displayed on an external display (e.g., display 103 illustrated in FIG. 1A) or stored in memory, in accordance with embodiments of the disclosure.

Block 480 is a loop to indicate whether another image should be processed or captured (e.g., for real-time display of the scene over time in the form of a video). If another combined color image of the scene is desired, block 480 proceeds to block 410 and the process repeats. If another image is not desired, block 480 proceeds to block 490 and the method 400 terminates.

Figures 4B, 4C:
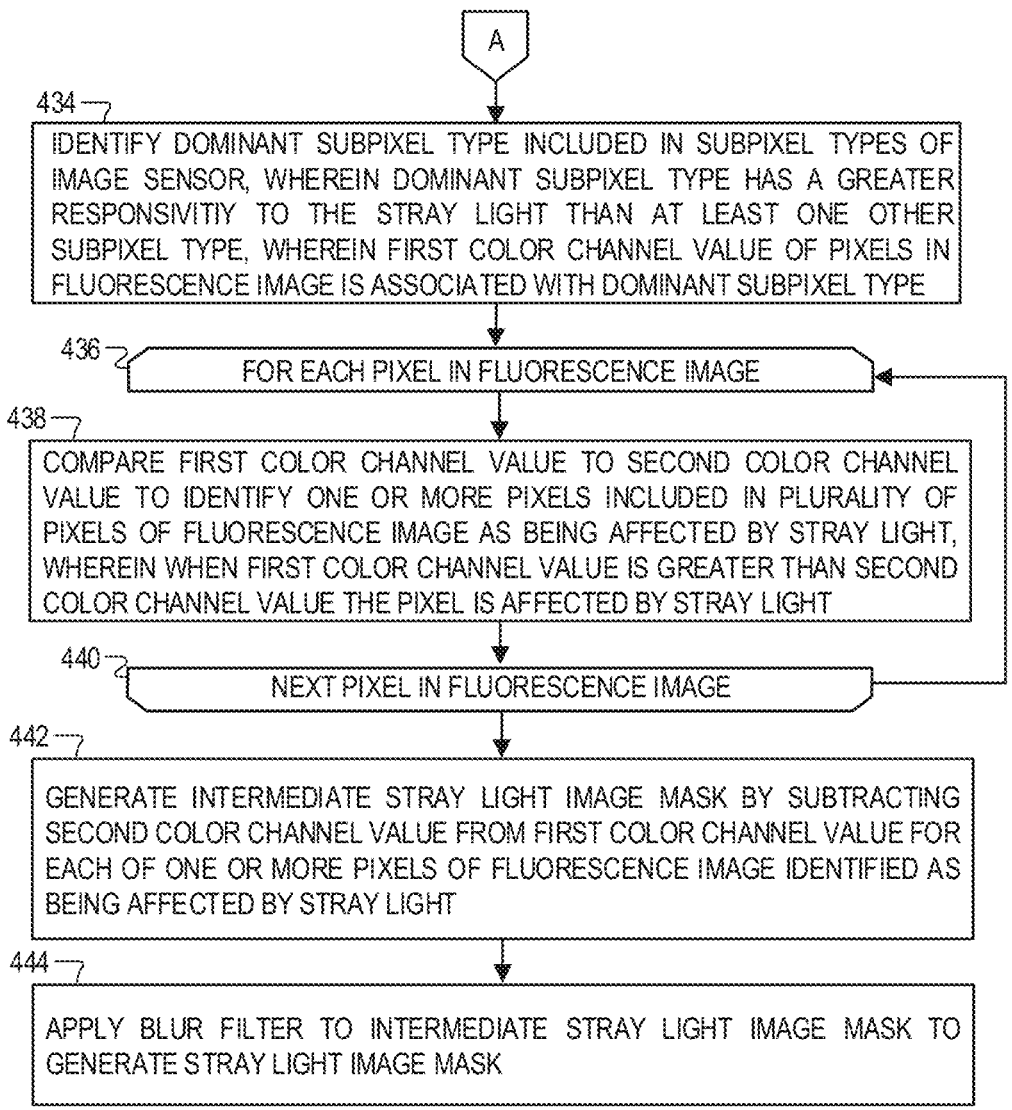
FIG. 4B illustrates an example process for generating a stray light image mask, in accordance with an embodiment of the disclosure.
FIG. 4C illustrates an example algorithm for generating the stray light image mask of FIG. 4B, in accordance with an embodiment of the disclosure.

FIG. 4B illustrates an example process 432 for generating a stray light image mask, in accordance with an embodiment of the disclosure. Process 432 may initiate upon receiving the fluorescence image generated in block 430 of method 400 illustrated in FIG. 4B.

Block 434 shows identifying a dominant subpixel type included in the subpixel types of the image sensor. The dominant subpixel type having a greater responsivity to the stray light than any other subpixel type included in the subpixel types. In one embodiment, the dominant subpixel type that is most responsive to stray light may be determined based on already known features (e.g., derived from known responsivity of the image sensor with respect to the known emission spectra of the excitation wavelength). In the same or other embodiments, the dominant subpixel type may be derived experimentally (e.g., by utilizing a calibration chamber where the only radiation source within the calibration chamber is the light source emitting the excitation wavelength, capturing a test image within the calibration chamber, and comparing color channel values of a given image pixel to determine the dominant subpixel type). In yet other embodiments, identification of the dominant subpixel type may be provided by a user of the system.

Block 436-440 illustrates a loop that looks at individual pixels of the fluorescence image to identify one or more pixels of the fluorescence image that are expected to be affected by stray light. As illustrated in FIG. 4B, the loop examines each pixel within the fluorescence image. However, it is appreciated that in some embodiments it may not be necessary to examine all pixels of the fluorescence image to generate a stray light image mask.

Block 438 shows comparing the first color channel value to the second color channel value of the given pixel of the loop to determine whether the given pixel is affected by stray light. In other words, block 438 is for identifying whether one or more pixels included in the plurality of pixels of the fluorescence image are affected by stray light. In some embodiments, the comparing of the first color channel value to the second color channel value of the given pixel is based on a difference in responsivity between subpixel types included in the image sensor. In one embodiment, the difference in responsivity is for stray light proximate to the excitation wavelength. In other words, the stray light is considered to be from the light emitted by the excitation source reflecting from the scene and becoming incident upon the image sensor. Thus, the responsivity difference is based on the responsivity of the image sensor proximate to the excitation wavelength (e.g., within 5%, 10%, 15%, 20%, or otherwise). In the same or other embodiments, the given pixel is identified as being affected by the stray light when the first color channel value is greater than the second color channel. In one embodiment the first color channel corresponds to a red color and is thus associated with red subpixel types of the image sensor and the second color channel corresponds to blue color and is thus associated with blue subpixel types of the image sensor.

Block 442 illustrates generating an intermediate stray light image by subtracting the second color channel value from the first color channel value for each of the one or more pixels of the fluorescence image identified as being affected by stray light. In other embodiments a ratio of the first color channel value with respect to the second color channel may be used to generate an intermediate stray light mask. It is appreciated that the intermediate stray light image mask may be represented by single color channel image pixels that are spatially associated with pixels of the fluorescence image. The single color channel values of the pixels of the intermediate stray light image mask that are spatially associated with the one or more pixels of the fluorescence image identified as being affected by the stray light are based on the difference between the first color channel value and the second color channel value, the ratio of the first color channel value with respect to the second color channel, or any other metric that reduces the influence of the stray light on the fluorescence image. It is appreciated that in some embodiments, single color channel values of the pixels included in the intermediate stray light mask that are not spatially associated with the one or more pixels of the fluorescence image identified as being affected by the stray light may have zero or null values.

Block 444 shows applying a blur filter to the intermediate stray light image mask to generate a stray light image mask. The blur filter may be a Gaussian blur, a step filter, a low-pass filter, a mean filter, a defocus blur, or any other type of blur technique to smooth the intermediate stray light image mask and generate the stray light image mask. In some embodiments, the stray light image mask is used to generate a revised fluorescence image with stray light reduction. However, in other embodiments block 444 may be optional and such the intermediate stray light image mask may also correspond to the stray light image mask used to generate the revised fluorescence image.

FIG. 4C illustrates an example algorithm for generating the stray light image mask for FIG. 4B, in accordance with an embodiment of the disclosure. As illustrated, the fluorescence image is represented by an array "ir" that includes red color channel values and blue color channel values for each element or pixel within the array. The intermediate mask is generated by comparing the difference between the red color channel value to the blue color channel value of a given element included in the array. If the red color channel value is greater than the blue color channel value of a given element, then the given element is identified as being affected by the stray light and the corresponding single color channel value of the intermediate image mask is calculated by subtracting the blue color channel value from the red color channel value. However, if the blue color channel value is greater then the red color channel value for the given element, then the corresponding single color channel value of the intermediate stray light image mask is a zero or null value. Finally, the stray light image mask is generated by applying a gaussian filter to the intermediate stray light image mask.

Figure 4D:
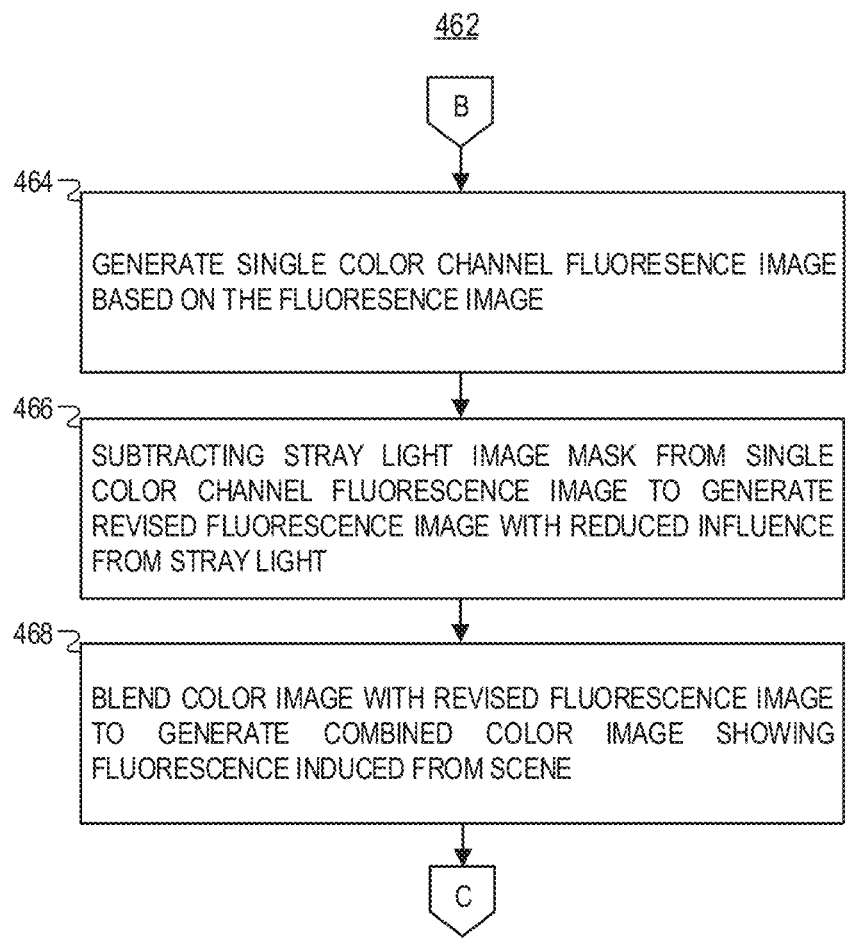
FIG. 4D illustrates an example process for generating a combined color image showing fluorescence induced from a scene with a reduced influence from stray light, in accordance with an embodiment of the disclosure.

FIG. 4D illustrates an example process 462 for generating a combined color image showing fluorescence induced from a scene with a reduced influence from stray light, in accordance with an embodiment of the disclosure. Process 462 may initiate upon receiving the color image generated in block 460 of method 400 illustrated in FIG. 4B and the stray light image mask generated in block 444 of FIG. 4B.

Block 464 shows generating a single color channel fluorescence image based on the fluorescence image received from block 430 of FIG. 4A. As discussed above, each pixel of the fluorescence image includes a first color channel value (e.g., associated with a red color based on the red subpixel type included in the image sensor), a second color channel value (e.g., associated with a blue color based on the blue subpixel type included in the image sensor), and a third color channel value (e.g., associated with a green color based on the green subpixel type included in the image sensor). In one embodiment, the single color channel fluorescence image is based on the third color channel values (e.g., green color) of the fluorescence image. In other embodiments, the single color channel fluorescence image may be based on other color channel values. In some embodiments, the single color channel fluorescence image may be based on an average of color channel values (e.g., the average of the first color channel value, the second color channel value, and the third color channel value).

Block 466 illustrates subtracting the stray light image mask from the single color channel fluorescence image to generate a revised fluorescence image with a reduced influence from the stray light. In some embodiments, the subtraction is done on a pixel-by-pixel basis. For example, a pixel in the first row and column of the stray light image mask may be subtracted from a pixel in the first row and column of the single color channel fluorescence image as said pixels are spatially associated with one another.

Block 468 illustrates blending the color image received from block 460 of FIG. 4A with the revised fluorescence image generated in block 466 of FIG. 4D to generate a combined color image showing a color image of the scene along with the fluorescence. In some embodiments, the revised fluorescence image is assigned a highlight color (e.g., green, blue, red, or any other color desired to be representative of fluorescence from the scene). In such an embodiment, the values of the revised fluorescence image may be normalized such that they are all within the range from zero to one. Then the normalized values of the revised fluorescence image are used to adjust the pixel values of the color image to generate the combined color image. For example, if a pixel in the first row and column of the revised fluorescence image is 0.5 and the highlight color is green, then the corresponding pixel of the color image is adjusted (e.g., interpolated) towards 50% green to generate the pixel in the first row and column of the combined color image. This process may be repeated for each pixel included in the combined color image.

The processes explained above are described in terms of computer software and hardware. The techniques described may constitute machine-executable instructions embodied within a tangible or non-transitory machine (e.g., computer) readable storage medium, that when executed by a machine (e.g., controller 130) will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system for fluorescence imaging of a scene, comprising:
    a light source to provide a first illumination of the scene, wherein during the first illumination the light source is configured to emit an excitation wavelength to induce fluorescence from the scene;
    an image sensor to capture a fluorescence image of the scene during the first illumination, wherein the fluorescence image includes a plurality of pixels, each pixel having at least a first color channel value and a second color channel value; and
    a controller coupled to the light source, the image sensor, and memory, wherein the memory includes instructions that when executed by the controller causes the system to perform operations including:
        comparing the first color channel value to the second color channel value of a given pixel for each of the plurality of pixels to identify one or more pixels included in the plurality of pixels of the fluorescence image as being affected by stray light; and
        generating a stray light image mask based, at least in part, on the one or more pixels of the fluorescence image identified as being affected by the stray light.

2. The system of claim 1, wherein the comparing of the first color channel value to the second color channel value is based on a difference in responsivity between subpixel types included in the image sensor.

3. The system of claim 2, wherein the difference in the responsivity between the subpixel types is for the stray light proximate to the excitation wavelength.

4. The system of claim 2, wherein the memory includes additional instructions that when executed by the controller causes the system to perform further operations, including:
    identifying a dominant subpixel type included in the subpixel types of the image sensor, wherein the dominant subpixel type has a greater responsivity to the stray light than any other subpixel type included in the subpixel types, and wherein the given pixel is included in the one or more pixels identified as being affected by the stray light when, during the comparing of the given pixel, the first color channel value is greater than the second color channel value.

5. The system of claim 4, wherein the stray light image mask includes a plurality of single color channel image pixels spatially associated with the plurality of pixels of the fluorescence image.

6. The system of claim 5, wherein the memory includes additional instructions that when executed by the controller causes the system to perform further operations, including:
    subtracting the second color channel value from the first color channel value for each of the one or more pixels of the fluorescence image identified as being affected by the stray light to calculate values for spatially associated pixels of the stray light image mask.

7. The system of claim 6, wherein regions of the stray light image mask that are not associated with the one or more pixels of the fluorescence image identified as being affected by the stray light have null values.

8. The system of claim 1, wherein the memory includes additional instructions that when executed by the controller causes the system to perform further operations, including:
    generating an intermediate stray light image mask by subtracting the second color channel value from the first color channel value for each of the one or more pixels identified as being affected by stray light; and
    applying a blur filter to the intermediate stray light image mask to generate the stray light image mask.

9. The system of claim 8, wherein the memory includes additional instructions that when executed by the controller causes the system to perform further operations, including:
    generating a single color channel fluorescence image based on the fluorescence image; and
    subtracting the stray light image mask from the single color channel fluorescence image to generate a revised fluorescence image with a reduced influence from the stray light.

10. The system of claim 9, wherein the single color channel fluorescence image is based on a third color channel value included in each of the plurality of pixels of the fluorescence image.

11. The system of claim 10, wherein the first color channel value, the second color channel value, and the third color channel value for each of the plurality of pixels are respectively associated with a red color, a blue color, and a green color.

12. The system of claim 9, wherein the memory includes additional instructions that when executed by the controller causes the system to perform further operations, including:
    configuring the light source to emit visible light to provide a second illumination of the scene;
    capturing a color image of the scene during the second illumination;
    blending the color image with the revised fluorescence image to generate a combined color image showing the fluorescence induced from the scene.

13. At least one machine-accessible storage medium that provides instructions that, when executed by a machine, will cause the machine to perform operations for fluorescence imaging of a scene, the operations comprising:

receiving a fluorescence image representative of the scene during fluorescence, wherein the fluorescence image includes a plurality of pixels, each pixel having at least a first color channel value and a second color channel value comparing the first color channel value to the second color channel value of a given pixel for each of the plurality of pixels to identify one or more pixels included in the plurality of pixels of the fluorescence image as being affected by stray light; and generating a stray light image mask based, at least in part, on the one or more pixels of the fluorescence image identified as being affected by the stray light.

14. The at least one machine-accessible storage medium of claim 13, wherein the comparing of the first color channel value to the second color channel value is based on a difference in responsivity between subpixel types included in an image sensor that captured the fluorescence image.

15. The at least one machine-accessible storage medium of claim 14, the difference in the responsivity between the subpixel types is for the stray light proximate to an excitation wavelength that induces the fluorescence from the scene.

16. The at least one machine-accessible storage medium of claim 14, further comprising additional instructions that, when executed by the machine, will cause the machine to perform further operations comprising:

identifying a dominant subpixel type included in the subpixel types of the image sensor, wherein the dominant subpixel type has a greater responsivity to the stray light than any other subpixel type included in the subpixel types, and wherein the given pixel is included in the one or more pixels identified as being affected by the stray light when, during the comparing of the given pixel, the first color channel value is greater than the second color channel value.

17. The at least one machine-accessible storage medium of claim 14, wherein the stray light image mask includes a plurality of single color channel image pixels spatially associated with the plurality of pixels of the fluorescence image.

18. The at least one machine-accessible storage medium of claim 17, further comprising additional instructions that, when executed by the machine, will cause the machine to perform further operations comprising:

subtracting the second color channel value from the first color channel value for each of the one or more pixels of the fluorescence image identified as being affected by the stray light to calculate values for spatially associated pixels of the stray light image mask.

19. The at least one machine-accessible storage medium of claim 18, wherein regions of the stray light image mask that are not associated with the one or more pixels of the fluorescence image identified as being affected by the stray light have null values.

20. The at least one machine-accessible storage medium of claim 13, further comprising additional instructions that, when executed by the machine, will cause the machine to perform further operations comprising:

generating an intermediate stray light image mask by subtracting the second color channel value from the first color channel value for each of the one or more pixels identified as being affected by stray light;

applying a blur filter to the intermediate stray light image mask to generate the stray light image mask;

generating a single color channel fluorescence image based on the fluorescence image; and subtracting the stray light image mask from the single color channel fluorescence image to generate a revised fluorescence image with a reduced influence from the stray light.

21. The at least one machine-accessible storage medium of claim 20, further comprising additional instructions that, when executed by the machine, will cause the machine to perform further operations comprising:

receiving a color image of the scene without the fluorescence; and blending the color image with the revised fluorescence image to generate a combined color image showing the fluorescence induced from the scene.

* * * * *